US009885962B2

(12) United States Patent
Veldman et al.

(10) Patent No.: US 9,885,962 B2
(45) Date of Patent: Feb. 6, 2018

(54) METHODS AND APPARATUS FOR MEASURING SEMICONDUCTOR DEVICE OVERLAY USING X-RAY METROLOGY

(71) Applicant: KLA-Tencor Corporation, Milpitas, CA (US)

(72) Inventors: Andrei Veldman, Sunnyvale, CA (US); Michael S. Bakeman, Union City, CA (US); Andrei V. Shchegrov, Campbell, CA (US); Walter D. Mieher, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 376 days.

(21) Appl. No.: 14/521,966

(22) Filed: Oct. 23, 2014

(65) Prior Publication Data

US 2015/0117610 A1    Apr. 30, 2015

Related U.S. Application Data

(60) Provisional application No. 61/896,230, filed on Oct. 28, 2013.

(51) Int. Cl.
*G01N 21/95* (2006.01)
*G03F 7/20* (2006.01)
*H01L 21/66* (2006.01)

(52) U.S. Cl.
CPC .......... *G03F 7/70633* (2013.01); *H01L 22/12* (2013.01); *G01N 21/9501* (2013.01)

(58) Field of Classification Search
CPC .................... G01N 21/9501; G03F 7/70633
See application file for complete search history.

(56) References Cited

U.S. PATENT DOCUMENTS

| 7,481,579 | B2 | 1/2009 | Yokhin et al. |
| 7,616,313 | B2 | 11/2009 | Kandel et al. |
| 7,929,667 | B1 | 4/2011 | Zhuang et al. |
| 61,893,341 | | 10/2013 | Bakeman |
| 8,879,073 | B2 | 11/2014 | Madsen et al. |

(Continued)

OTHER PUBLICATIONS

"Int'l Application Serial No. PCT/US2014/062674, Search Report & Written Opinion dated Jan. 27, 2015", 11 pgs.

(Continued)

*Primary Examiner* — Dani Fox
(74) *Attorney, Agent, or Firm* — Kwan & Olynick, LLP

(57) ABSTRACT

Disclosed are apparatus and methods for determining overlay error in a semiconductor target. For illumination x-rays having at least one angle of incidence (AOI), a correlation model is obtained, and the correlation model correlates overlay error of a target with a modulation intensity parameter for each of one or more diffraction orders (or a continuous diffraction intensity distribution) for x-rays scattered from the target in response to the illumination x-rays. A first target is illuminated with illumination x-rays having the at least one AOI and x-rays that are scattered from the first target in response to the illumination x-rays are collected. An overlay error of the first target is determined based on the modulation intensity parameter of the x-rays collected from the first target for each of the one or more diffraction orders (or the continuous diffraction intensity distribution) and the correlation model.

22 Claims, 11 Drawing Sheets

(56) References Cited

U.S. PATENT DOCUMENTS

| | | | |
|---|---|---|---|
| 2007/0224518 A1* | 9/2007 | Yokhin | G03F 7/70633 |
| | | | 430/5 |
| 2008/0137810 A1 | 6/2008 | Liu et al. | |
| 2011/0080585 A1 | 4/2011 | Rabello et al. | |
| 2011/0280530 A1 | 11/2011 | Verman et al. | |
| 2013/0155406 A1* | 6/2013 | Den Boef | G03F 7/70633 |
| | | | 356/401 |
| 2013/0304424 A1 | 11/2013 | Bakeman et al. | |
| 2015/0110249 A1 | 4/2015 | Bakeman et al. | |

OTHER PUBLICATIONS

Jones, Ronald L. et al., "Cross Section and Critical Dimension Metrology in Dense High Aspect Ration Patterns with CDSAXS", AIP Conference Proceedings 788, 403, Accessed on the Internet: <http://scitation.aip.org/content/aip/proceeding/aipcp/10.1063/1.2062994>, 2005, 5 pgs.

\* cited by examiner

METHODS AND APPARATUS FOR MEASURING SEMICONDUCTOR DEVICE OVERLAY USING X-RAY METROLOGY

CROSS-REFERENCE TO RELATED APPLICATIONS

This application claims the benefit of prior application U.S. Provisional Application No. 61/896,230, filed 28 Oct. 2013 by Andrei Veldman et al., which application is herein incorporated by reference in its entirety for all purposes.

TECHNICAL FIELD OF THE INVENTION

The present invention relates generally to methods and systems for semiconductor metrology and, more specifically, to overlay metrology.

BACKGROUND

Photolithography or optical lithography systems used in the manufacture of integrated circuits have been around for some time. Such systems have proven extremely effective in the precise manufacturing and formation of very small details in the product. In some photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with a material sensitive to irradiation, e.g., photoresist. The exposed photoresist typically forms a pattern that after development masks the layers of the wafer during subsequent processing steps, as for example deposition and/or etching.

Due to the large scale of circuit integration and the decreasing size of semiconductor devices, the reticles and fabricated devices have become increasingly sensitive to overlay errors, as well as other critical parameter variations such as critical dimension variations, etc. These variations, if uncorrected, can cause the final device to fail to meet the desired performance due to electrical timing errors. Even worse, these errors can cause final devices to malfunction and adversely affect yield.

Improved apparatus and techniques for determining overlay error, and the like, on a semiconductor target are desired.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for determining overlay error in a semiconductor target is disclosed. For illumination x-rays having at least one angle of incidence (AOI), a correlation model is obtained, and the correlation model correlates overlay error of a target with a modulation intensity parameter for each of one or more diffraction orders or a continuous diffraction intensity distribution for x-rays scattered from the target in response to the illumination x-rays. A first target is illuminated with illumination x-rays having the at least one AOI and x-rays that are scattered from the first target in response to the illumination x-rays are collected. An overlay error of the first target is determined based on the modulation intensity parameter of the x-rays collected from the first target for each of the one or more diffraction orders or the continuous diffraction intensity distribution and the correlation model.

In a specific implementation, the modulation intensity parameter is an intensity minimum for each of one or more diffraction orders, in Qz, where Qz is an intensity measurement of the collected x-rays as a function of at least one AOI. In another aspect, the correlation model is determined by a neural network or a principal component analysis. In another example, the first target is aperiodic.

In a particular embodiment, the overlay is determined for a first direction, and the method further includes repeating the operations for illuminating and determining a second overlay error in a second direction that differs from the first direction. In one aspect, the first target is illuminated with illumination x-rays at a plurality of different AOIs. In a further aspect, illuminating at the different AOIs is accomplished simultaneously. In another aspect, illuminating at the different AOIs is accomplished sequentially.

In a specific example, the first target comprises two or more vertically stacked gratings. In another example, the first target is designed to have pitch and critical dimension values that meet device design rule specifications. In a further aspect, the first target is located in an active device and in-die area. In specific implementations, illuminating and collecting are performed by a transmission small-angle x-ray scattering (T-SAXS) system, a grazing incident small-angle x-ray scattering (GI-SAXS) system, a wide angle x-ray scattering (WAXS) system, an x-ray diffraction (XRD) system, grazing incidence x-ray diffraction (GIXRD) system, or a high resolution x-ray diffraction (HRXRD) system.

In an alternative embodiment, the invention pertains to a semiconductor metrology system. The system includes an x-ray source for generating x-rays and illumination optics for collecting and reflecting or refracting a portion of the generated x-rays towards a particular focus point on a semiconductor sample in the form of a plurality of incident beams at a plurality of different angles of incidence (AOIs). The system further includes a sensor for collecting output x-ray beams that are scattered from the sample in response to the incident beams on the sample at the different AOIs and a controller configured for performing one or more of the above described method embodiments. For example, the controller is configured for (i) obtaining, for illumination x-rays having at least one angle of incidence (AOI), a correlation model that correlates overlay error of a target with a modulation intensity parameter for each of one or more diffraction orders (or a continuous diffraction intensity distribution) for x-rays scattered from the target in response to the illumination x-rays; (ii) causing the illumination optics to illuminate a first target with illumination x-rays having at least one AOI and collecting x-rays that are scattered from the first target in response to the illumination x-rays, and (iii) determining an overlay error of the first target based on the modulation intensity parameter of the x-rays collected from the first target for each of the one or more diffraction orders (or the continuous diffraction intensity distribution) and the correlation model.

These and other aspects of the invention are described further below with reference to the figures.

BRIEF DESCRIPTION OF THE DRAWINGS

FIG. 7 is a flow chart illustrating a procedure for determining overlay using displacement of local modulation in a $Q_z$ plot in accordance with one embodiment of the present invention.

FIG. 8 is a side view of three gratings.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Certain embodiments of the present invention may be implemented with respect to a scatterometry apparatus with small angle x-ray scattering (SAXS) capabilities. This system may include a high brightness x-ray source coupled with a high efficiency x-ray illumination system with improved measurement capabilities. A SAXS system is capable of measuring geometric parameters in semiconductor structures such as overlay, pitch, critical dimensions (CD), height, side wall angle (SWA), line-width roughness (LWR), line-edge roughness (LER), pitch walk, etc. The measured features can also be smaller than 10 nm. In addition, the high energy nature of x-ray radiation allows for the penetration of x-rays into optically opaque thin films, buried structures, high-aspect ratio structures and devices containing many thin film layers.

Figure 1:
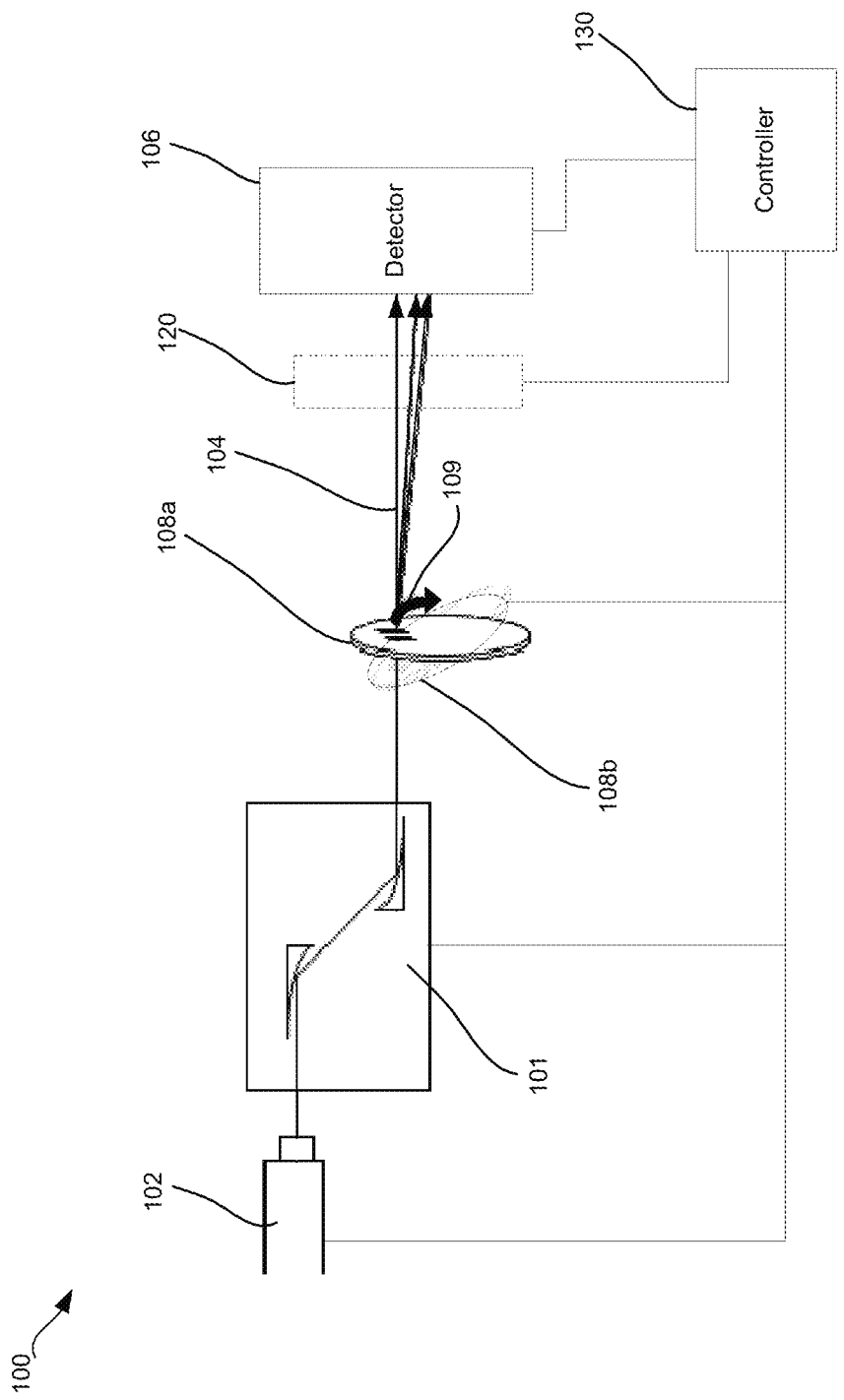
FIG. 1 is a diagrammatic side view of a transmission small angle x-ray scattering (T-SAXS) illumination system, in which techniques of the present invention may be implemented in accordance with one embodiment of the present invention.

FIG. 1 is a diagrammatic side view of a transmission small angle x-ray scattering (T-SAXS) illumination system 100, in which techniques of the present invention may be implemented in accordance with one embodiment of the present invention. The SAXS system 100 may include one or more x-ray sources 102 with suitable x-ray photon energies for generating the X-rays that are incident on and penetrate a sample 108a. In one embodiment, a high brightness x-ray source may include a solid anode X-ray source, a liquid metal jet X-ray source, and liquid droplet X-ray source, or other bright x-ray sources such as an Inverse-Compton x-ray source.

Additionally, the system 100 may include any suitable illumination x-ray optics 101 for directing and conditioning incident x-rays to impinge and penetrate the sample 108. For instance, the x-ray beams may be collimated or focused and/or monochromatized by the illumination x-ray optics 101 and then incident on the sample 108.

The sample 108a can be tilted (e.g., via a stage in rotation direction 109) to achieve different AOIs. Different tilt positions in directions 109 for the sample will result in different AOIs with respect to the specific x-rays that are reflected from the illumination optics 101. For instance, sample 108b is shown at a second tilt position with respect to first position sample 108a.

The scattered x-rays 104 may be collected by one or more x-ray detectors 106, while a sample handler holds the sample 108a and translates and/or rotates the sample 108a for positioning and alignment and to produce angularly resolved scattered x-rays 104.

The detector can be any suitable sensor for detecting scattered x-rays and generating a resulting spectra or image. By way of examples, the sensor can include one or more of the following: a photodiode array, a Charged Coupled Device (CCD), image plate, a hybrid pixel CCD, etc. The detector generally produces an intensity signal that can then be converted to an image by the detector (or controller 130).

Certain embodiments of the present invention include techniques for measuring overlay error. These techniques may take advantage of the vertical stacking of the parts of a semiconductor device in which overlay error is to be measured. In general, the vertical stacking affects the x-ray diffracted signal in a strong and unique way when measurements are made at one or more incidence directions for the illuminating x-ray beam relative to the plane of the semiconductor wafer.

A model building and analysis engine can be used to create models of the samples incorporating geometric and material properties of the sample. The models can be used to produce optical and x-ray simulations. Optical simulations can be based, e.g. upon rigorous coupled-wave analysis (RCWA), which are based on Maxwell's equations that are solved to calculate optical signals, such as scattering and/or reflectivities for different polarizations, ellipsometric parameters, phase change, etc. X-ray scattering simulations can be based upon x-ray form factors:

$$F(\vec{q}) = \int \rho(\vec{r}) e^{-i\vec{q}\cdot\vec{r}} d\vec{r}$$

where F is the form factor, q is the scattering vector, and ρ(r) is the electron density of the sample. The x-ray scattering intensity is then given by $$I(\vec{q}) = F^*F,$$

as described further in the publication by R. L. Jones et. al., "Cross Section and Critical Dimension Metrology in Dense High Aspect Ratio Patterns with CD-SAXS", which publication is incorporated herein by reference.

The analysis engine may be used to compare the simulated x-ray and optical scattering with the measured data so as to determine geometric, as well as material, properties of the sample. This modeling engine can be used in an embodiment of this invention, but such modeling engine is not mandatory. Certain embodiments of the present invention can be used without fully modeling the structure and its interaction with the x-rays. The descriptions below regarding simulation results using such an engine are not meant to limit the scope of the invention.

Figure 2A:
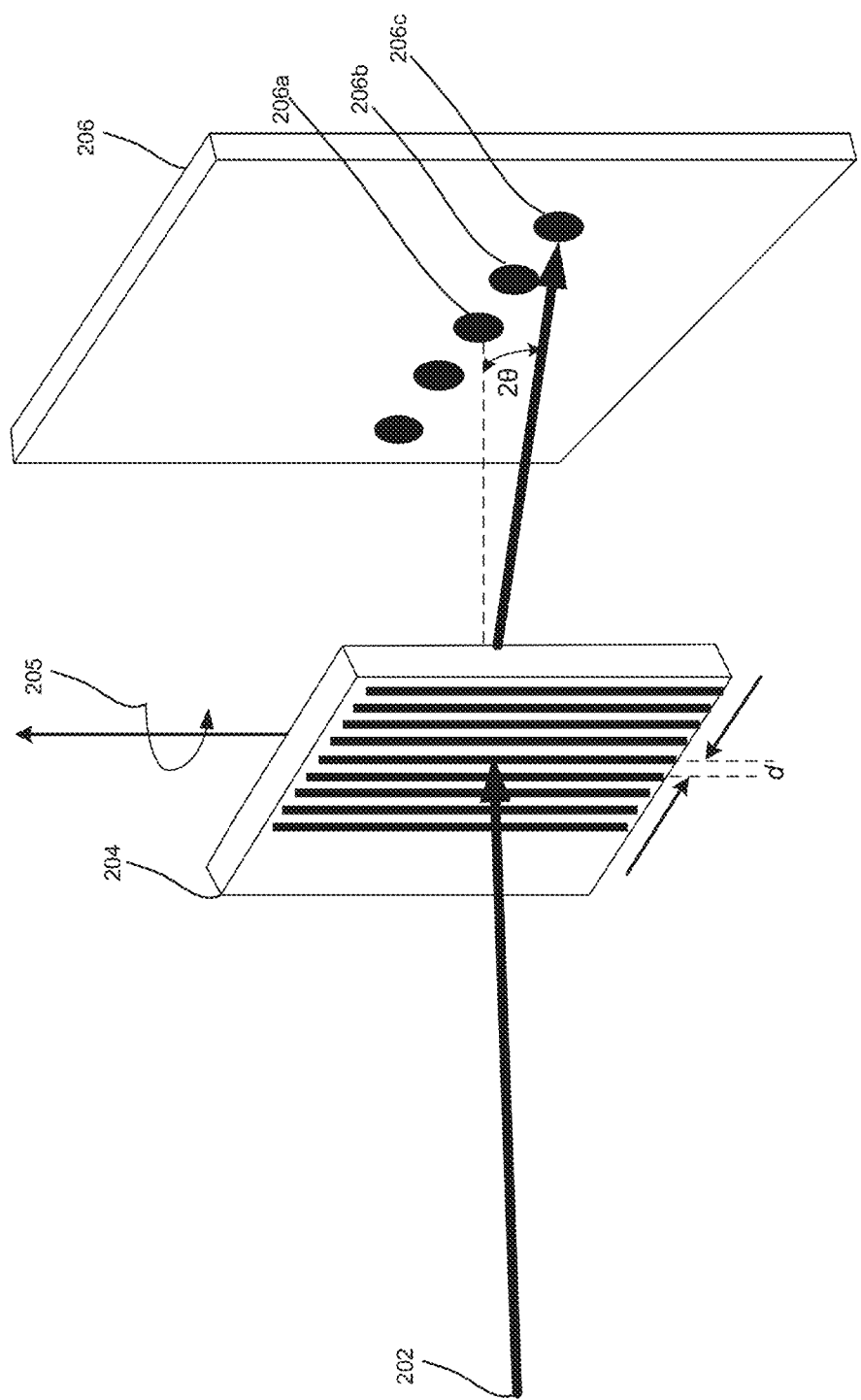
FIG. 2A illustrates a scattering vector $Q_x$ or output diffraction pattern for a normal AOI.

For a normal incidence x-ray beam, the scattered x-rays can be represented with a $Q_x$ value. In general, the scattering across the detector for a normal incident AOI can be represented by $Q_x$. FIG. 2A illustrates a scattering vector $Q_x$ or output diffraction pattern for a normal AOI. Incident x-ray beam 202 is transmitted through sample 204 having a grating with period d. The incident x-ray beam 202 results in a diffraction pattern on detector 206. For instance, the diffraction pattern contains a 0 order 206a, $1^{st}$ order 206b, and a $2^{nd}$ order 206c. The angle between the specular or 0 order and a scattered non-zero order is represented by N. Although not shown, generally speaking the intensity for the orders farther away from the zero order will be less intense than the orders closer to the zero order.

Figure 2B:
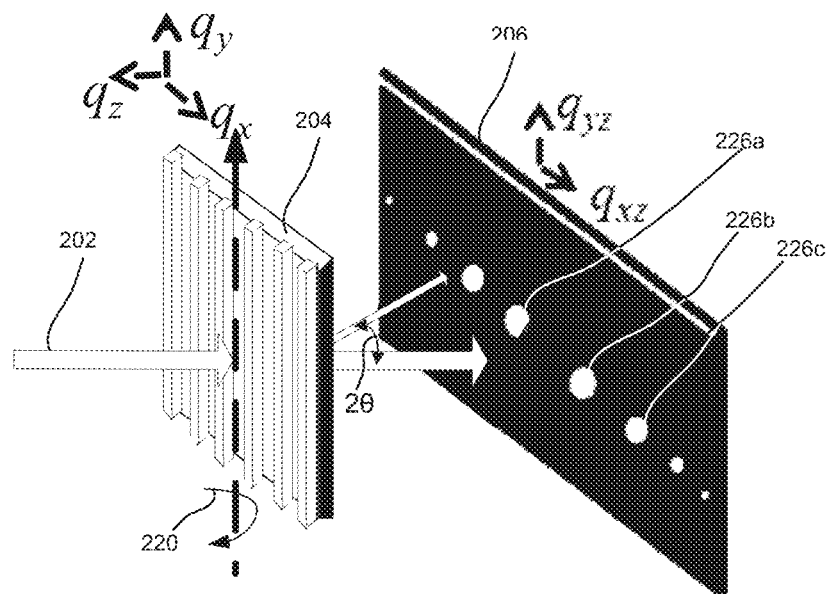
FIG. 2B illustrates $Q_z$ scattering vectors for a non-normal AOI in accordance with one embodiment of the present invention.

Rotation of the sample to different AOI's (e.g., in direction 205) can then result in different diffraction patterns that can be mapped with respect to both a $Q_x$ and a $Q_z$ axis. FIG. 2B illustrates $Q_z$ scattering vectors for a non-normal AOI in accordance with one embodiment of the present invention. As shown, the sample 204 is rotated by angle $\Phi$ (220) to produce a diffraction pattern (e.g., 226a, 226b, and 226c) on the detector 206.

Different AOIs will result in differences in the diffraction pattern on the detector, both in intensity and relative positions of the diffraction orders. For instance, the diffraction orders will be more spread out or more compact with different intensities for the different AOIs.

Figure 2C:
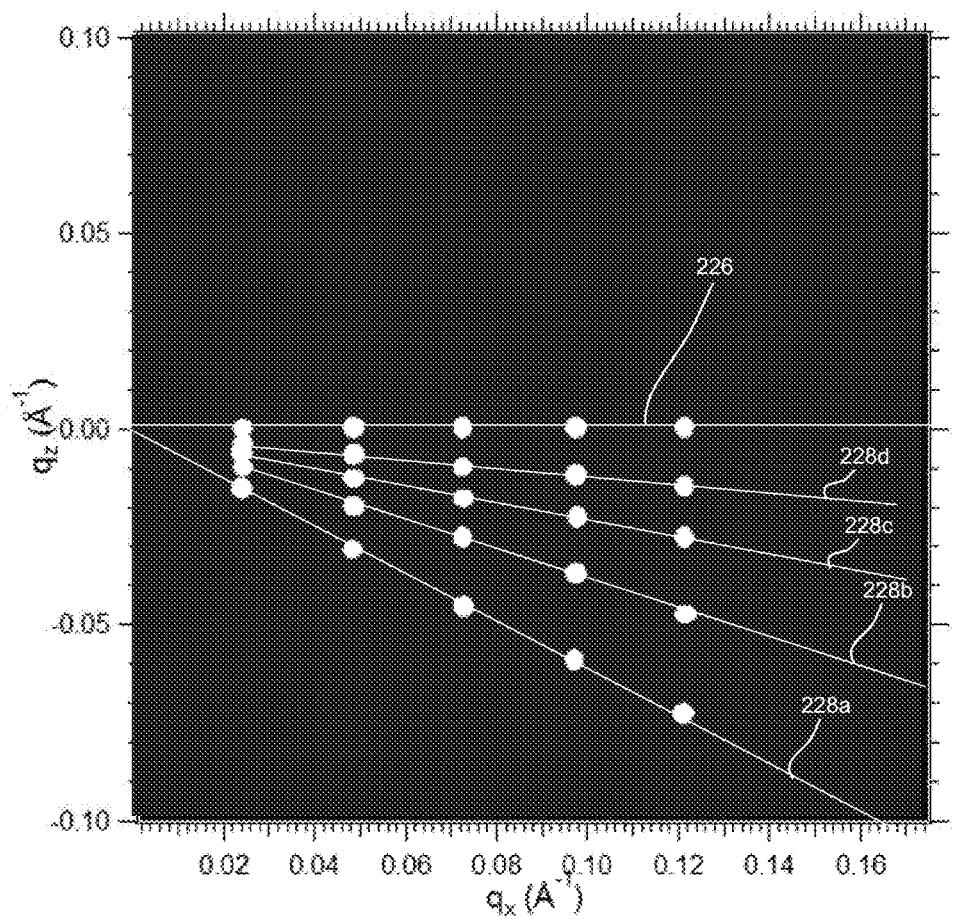
FIG. 2C illustrates simplified mapping of x-ray diffraction patterns for different AOI's into a two dimensional space that includes $Q_x$ and a $Q_z$ axis in accordance with one embodiment of the present invention.
Figure 3B:
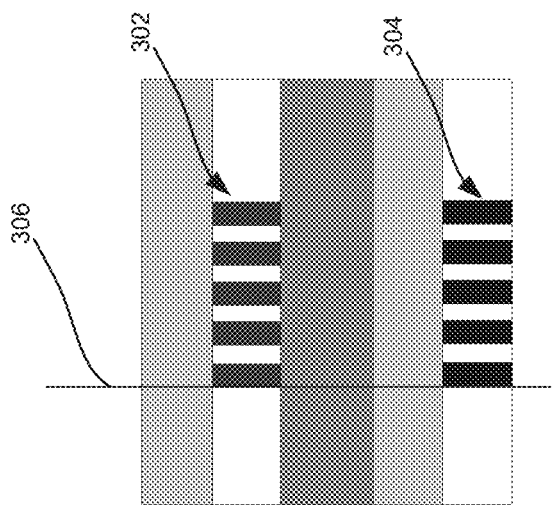
FIG. 3B is a side view of two gratings with zero overlay error.
Figure 3A:
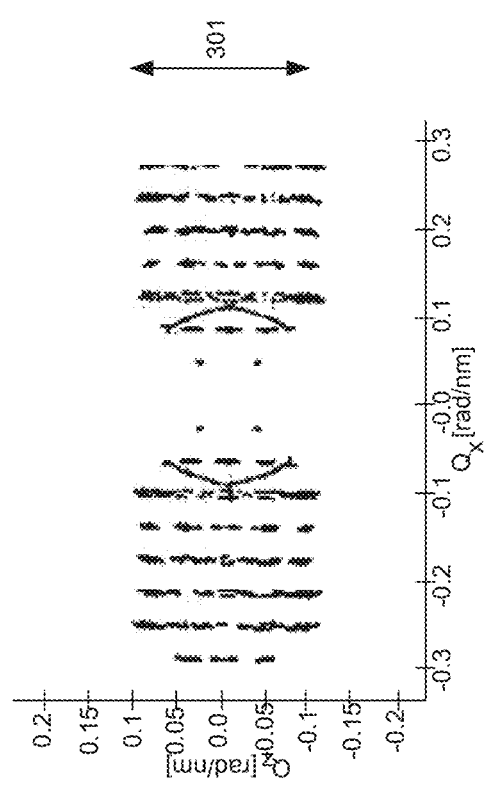
FIG. 3A shows the diffraction patterns for a plurality of AOIs mapped onto a $Q_z$ and Qx axis for a target having zero overlay error.

FIG. 2C illustrates simplified mapping of x-ray diffraction patterns for different AOI's into a two dimensional space that includes $Q_x$ and a $Q_z$ axis in accordance with one embodiment of the present invention. Each diffraction pattern for each of a plurality of AOIs is shown. For instance, the diffraction data points for a first AOI are shown along line 228a, while the diffraction points for a second AOI are shown along line 228b. Data on line 228a may correspond to the diffraction pattern at 150° $\Phi$ (or AOI). Likewise, the diffraction points for a third and fourth AOI are shown along lines 228c and 228d, respectively. The normal AOI diffraction points are shown along horizontal line 226, which corresponds to the normal $Q_x$ axis. For the different AOI's ($\Phi$), the different diffraction measurements are rotated and plotted in a $Q_z$ and $Q_x$ graph to obtain a fan of rotated diffraction data. By way of further explanation, $Q_x$ corresponds to intensity as a function of detector position (or I(x)), while $Q_z$ corresponds to the intensity as a function of detector position I(x) which is plotted along a rotated axis that corresponds to the specific AOI angle, which is relative to the normal or $Q_x$ axis. The diffraction data for each AOI is plotted for each corresponding AOI or ray to build up a $Q_x$-$Q_z$ map Overlay error can affect the scattered data when mapped into the $Q_z$ axis. For instance, a higher frequency modulation in the orders is seen with respect to the $Q_z$ axis when there is an overlay error, as compared with zero overlay error. FIG. 3A shows the diffraction patterns for a plurality of AOIs mapped onto a $Q_z$ axis for a target having zero overlay error. FIG. 3B is a side view of two gratings 302 and 304 with zero overlay error. That is, the gratings 302 and 304 are aligned, for example, along line 306.

Note the vertical modulation (local intensity maxima separated by local minima) (along $Q_z$ axis) within each diffraction order, for example, as shown in FIG. 3A, can be observed if data is collected at one or more non-normal incidence directions.

Figure 4B:
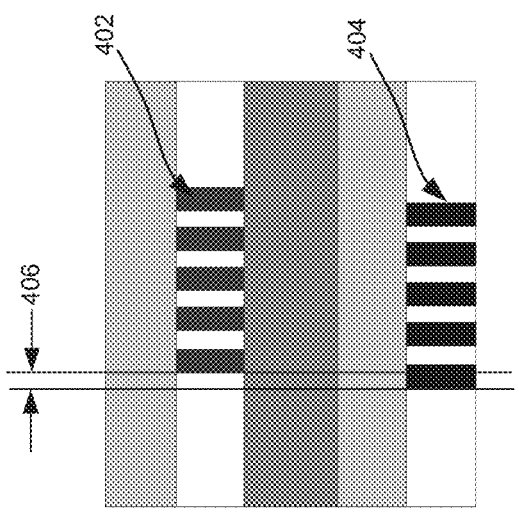
FIG. 4B is a side view of two gratings with an overlay error.
Figure 4A:
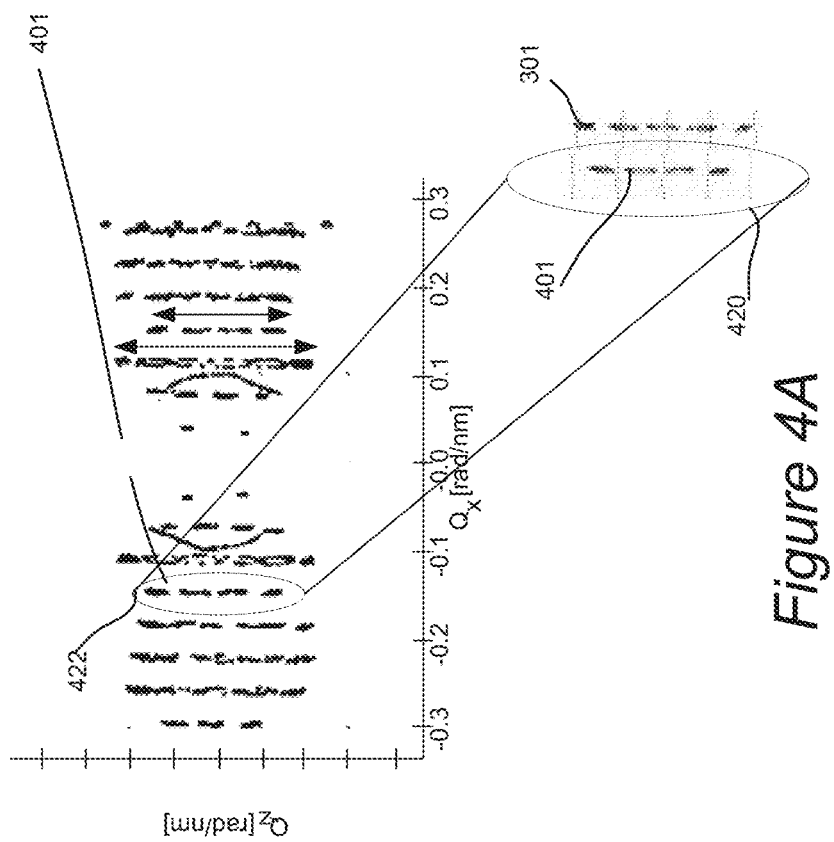
FIG. 4A shows the diffraction patterns for a plurality of AOIs mapped onto a $Q_z$ and Qx axis for a target having an overlay error.

These vertical modulations in the $Q_z$ direction also depend on the amount of overlay. That is, the vertical modulations are stretched are compressed in the presence of an overlay error, as compared with vertical modulation for a zero overlay error. For instance, FIG. 4A shows the diffraction patterns for a plurality of AOIs mapped onto a $Q_z$ axis for a target having an overlay error (406 of FIG. 4B). As shown in FIG. 4B, the target is formed from gratings 402 and 404, which are shifted relative to one another by overlay error amount 406. As shown, some of the diffraction data has a change in the $Q_z$ modulation (e.g., 401), as compared to the zero overlay diffraction data (e.g., 301 of FIG. 3A). As shown, the position of the local minima (modulation within diffraction orders) in FIG. 4A has shifted noticeably in the presence of an overlay error, relative to their position at zero overlay error as shown in FIG. 3A. Specifically, area 420 corresponds to area 422 on the plot, having modulation in the vertical direction for a particular set of $Q_z$ data 401. This particular set of $Q_z$ data 401 for an overlay error (406) is shown next to the corresponding set of $Q_z$ data 301 for zero overlay error to illustrate the minima shift.

In this example, each vertical set of $Q_z$ data pertains to at least two diffraction orders with particular modulations. These modulations for vertical set of data 301 have minima for the different diffraction orders that align when there is zero overlay, while the modulations for the vertical set of data 401 have minima for the different diffraction orders that are shifted relative to each other in the presence of overlay error.

Figure 5A:
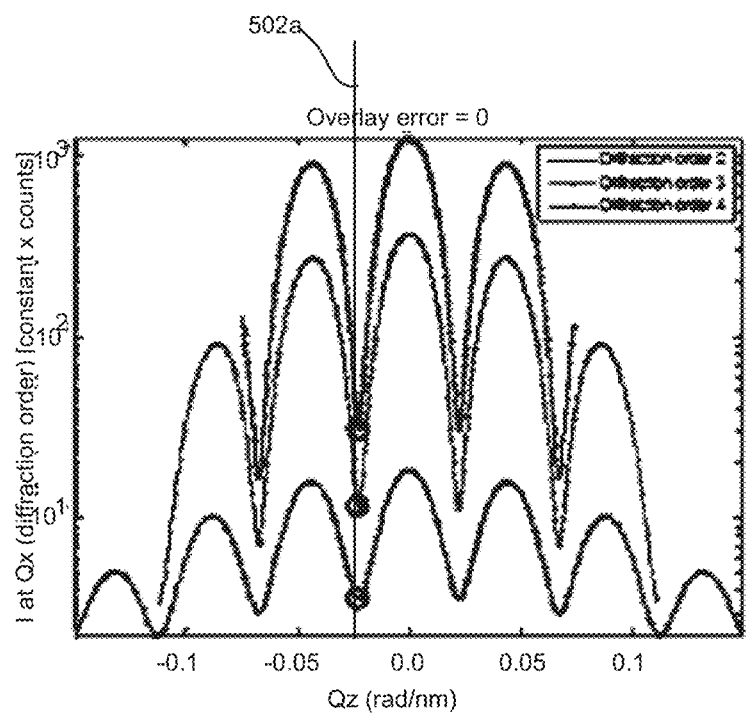
FIG. 5A through 5G are plots of the intensity distribution within each of three diffraction orders as a function of $Q_z$ in accordance with a specific implementation of the present invention.
Figure 5B:
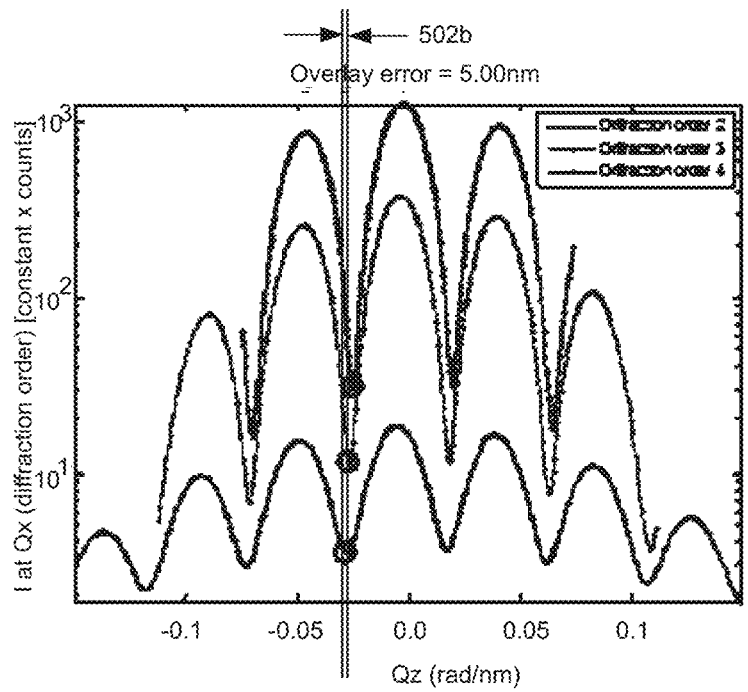
Figure 5C:
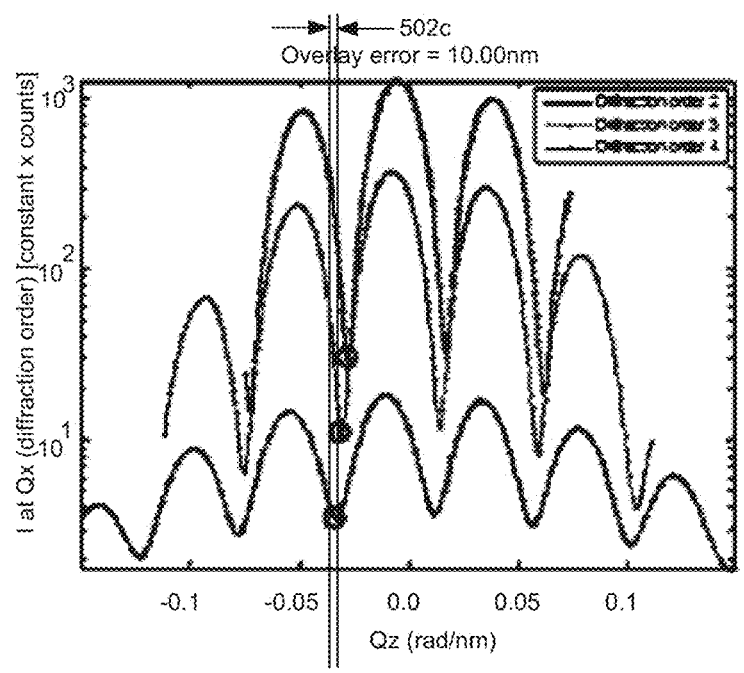
Figure 5D:
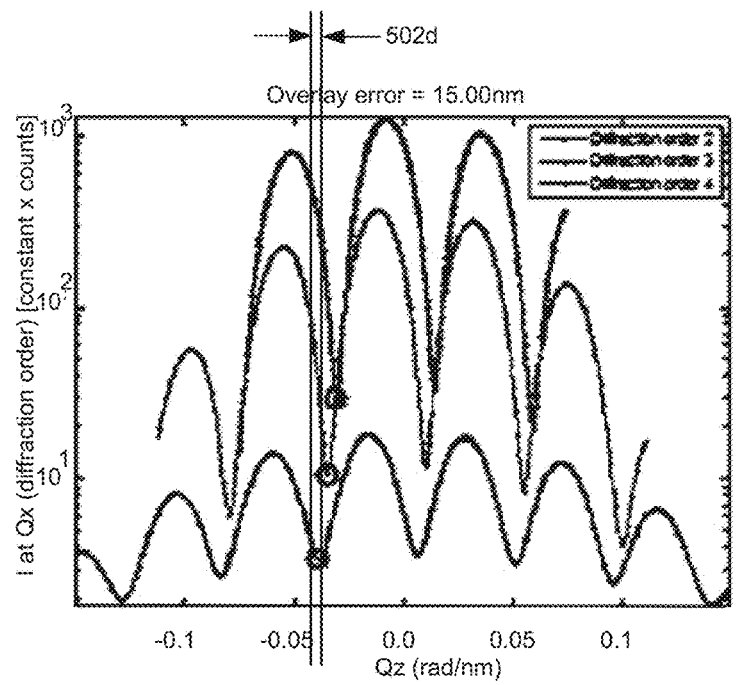
Figure 5E:
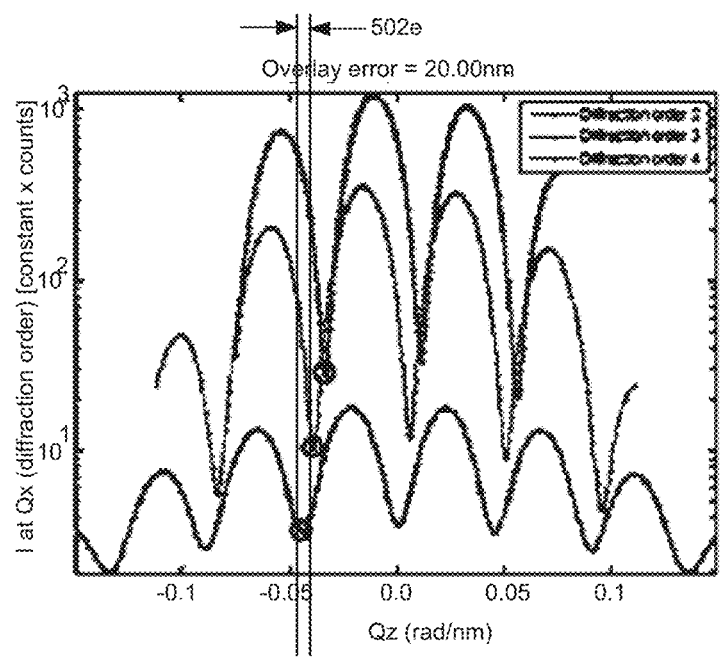
Figure 5F:
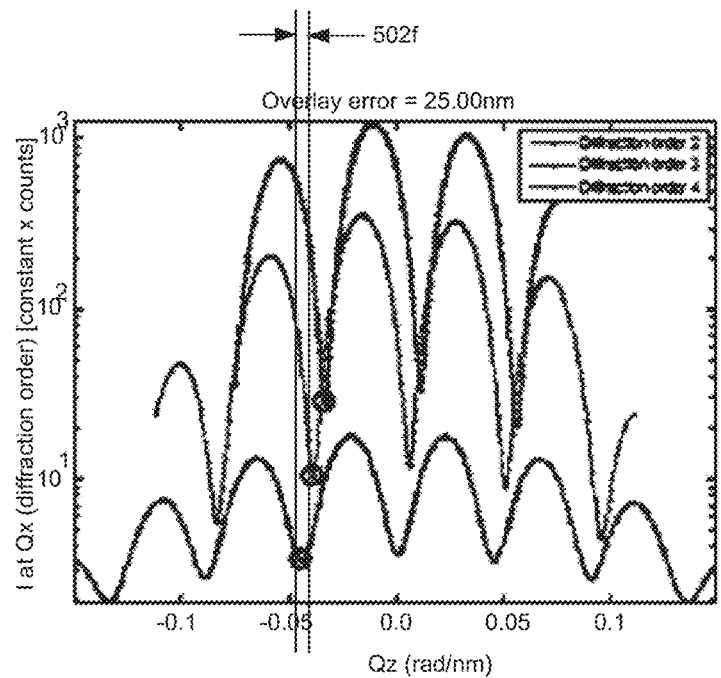
Figure 5G:
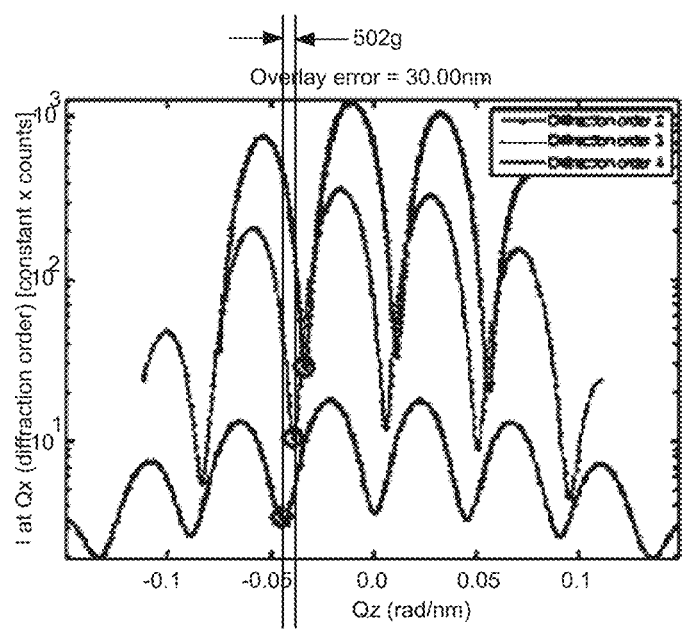

To illustrate this local minima shift more clearly, the following plots (FIG. 5A through 5G) show intensity distribution within each of three diffraction orders (2, 3 and 4) as a function of $Q_z$ in accordance with a specific implementation of the present invention. The location of a specific local modulation minimum is marked by a black circle. The amount of overlay error is specified above each plot. As illustrated, the overlay error value results in different minima shift amounts for the different diffraction orders. As shown in FIG. 5A, zero overlay error results in no minima shift (e.g., 502a). In contrast, different minima shifts 502b, 502c, 502d, 502e, 502f, and 502g are present between the $3^{rd}$ and $4^{th}$ orders for different overlay errors 5, 10, 15, 20, 25, and 30 nm, respectively, as shown in FIGS. 5B-5G. Different minima shifts are also present between other pairs of diffraction orders (e.g., $2^{nd}$ and $3^{th}$).

Figure 6:
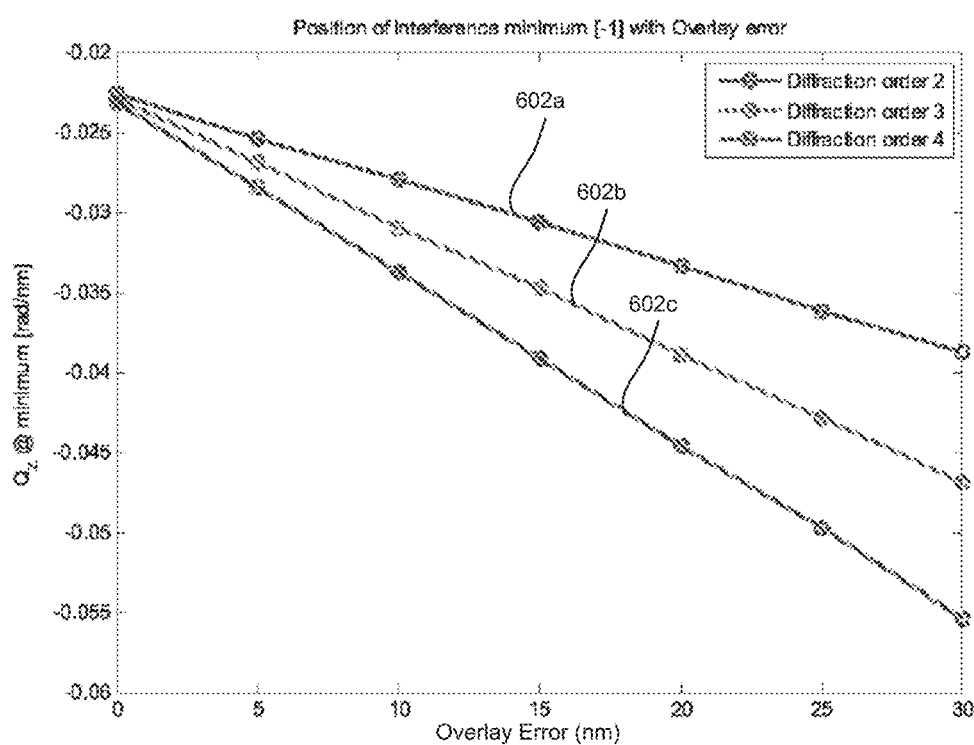
FIG. 6 illustrates a plot of the $Q_z$ minima intensity values for three different diffraction orders as a function of overlay error in accordance with one implementation of the present invention.

The overlay error can be determined quantitatively with good precision and accuracy by correlating the modulation minima for a plurality of diffraction orders to an overlay error value without performing costly full simulations. FIG. 6 illustrates a plot of the $Q_z$ minima intensity values for three different diffraction orders (including a $2^{nd}$ order 602a, a $3^{rd}$ order 602b, and a $4^{th}$ order 602c) as a function of overlay error. In this example, the minima position for the $4^{th}$ diffraction order seems more sensitive to overlay error. Since the displacement of the modulation minima for different overlay errors is linear, overlay error can be determined from each particular displacement of such minima. For instance, overlay error can be calculated, in principal, based on two different $Q_z$ minima values. Thus, techniques of the present invention allow a very accurate overlay error determination from a low number of measurements.

FIG. 7 is a flow chart illustrating a procedure 700 for determining overlay using displacement of local modulation in a $Q_z$ plot in accordance with one embodiment of the present invention. Initially, for at least one non-normal AOI, a model that correlates minima $Q_z$ values for one or more diffraction orders (or a continuous diffraction intensity distribution) and overlay error is obtained in operation 702. That is, $Q_z$ minima positions for different overlay errors for a particular target structure and at least one AOI may be modeled. For instance, incident x-rays at a plurality of AOIs on a particular target structure with different overlay errors and the resulting $Q_z$ minima values may be modeled.

In more general terms, any suitable intensity modulation parameter for each of a plurality of diffraction orders for x-rays scattered from a target, in response to illumination x-rays having at least one AOI, may be correlated with overlay error. In the present example, a correlation between overlay error and minima intensity $Q_z$ values is determined for each diffraction order. However, a correlation may also be determined for each maxima value, etc.

The target may then be illuminated with a plurality of incident x-ray beams at a plurality of AOIs in operation 702. Output x-ray beams that are scattered from the target in response to the incident x-ray beam are also collected in operation 704. The output beams for the different AOIs may be collected sequentially or simultaneously, depending upon the particular metrology tool's capabilities.

The AOIs may be selected so as to optimize sensitivity to overlay error and minimize correlation of the overlay error and CD. This optimization may be determined through any suitable modeling technique. A narrow range of AOIs (or even a single non-normal AOI) may be selected. This optimization can be accomplished by modelling the scattering from the particular overlay structures at a number of different AOIs and selecting a range of AOIs for which the sensitivity to overlay is the greatest.

A $Q_z$ map may then be determined based on the collected output x-ray beams that are scattered from the target in operation 706. The overlay error may then be determined based on the $Q_z$ minima between one or more pairs of diffraction orders using the correlation model in operation 708. Said in another way, the overlay error can be determined based on two or more local minima values in the $Q_z$ space.

Also, it has been found that the displacement of the local modulation minima with overlay error is decoupled from the CD, as well as other structure parameters, of the target structure. That is, CD or other structure parameter changes do not manifest as high frequency modulations in $Q_z$. Since the correlation of the overlay parameter with the CD or other structure parameters is essentially zero, overlay error is linearly independent from them. Therefore, the overlay error can be extracted without doing a full modeling of the target and its interaction with the x-ray radiation, but rather by using a model-free algorithmic approach, for example a neural network, or using a Principal Component Analysis, where the overlay parameter is substantially one of the principal components.

The modulation described above will also occur even if the two parts of the target for which overlay error is being measured are aperiodic (in one or more directions). In this case, although there will be no distinct diffraction orders along the horizontal Qx axis, the modulation in the vertical direction (Qz) of the same plots will still occur and the position of maxima and minima will change with the overlay error.

The above described techniques can also be used to measure overlay in two different directions x and y. For instance, the wafer can initially be rotated about an axis (e.g., 109) to collect diffraction patterns in a Qz, Qx map. The modulation in the diffraction pattern of Qz at a constant Qx can be used to determine the overlay offset in the x direction. Likewise, the wafer can then be rotated about an orthogonal angle, and the collected diffraction pattern can then be obtained in a Qz, Qy map. The modulation in the diffraction pattern of Qz at a constant Qy will determine the overlay offset in the y direction. In this manner, both x and y overlay offsets can be determined.

Compared to optical overlay measurement methods, techniques that utilize displacement of $Q_z$ minima allow measurement at design rule pitch (not having to have a large pitch requirement), thus, reflecting the real device overlay much more faithfully. In fact, certain inventive techniques work better with smaller pitches.

Certain embodiments of the present invention may be applied to device structures in the active device area, as well as specific overlay targets within the scribe lines. Additionally, both negative and positive overlay errors can be distinguished from each other (e.g., by correlating both negative and positive overlay errors with modulation parameters, such as minima values). Certain embodiments of the present invention also do not require a periodic target. Compared to SEM overlay, the x-ray overlay techniques described herein can detect overlay for targets at various depths and is non-destructive. Certain embodiments described herein can measure with good accuracy and precision overlay decoupled from CD. Additionally, external reference CD metrology or costly and difficult full modeling is not required. The above described techniques also result in de-correlation of the CD parameters themselves, thus enhancing other x-ray CD measurements, and providing simultaneous x-ray information.

It should be noted that techniques of the present invention are not limited to measuring overlay between only two gratings, but is also extendable to three or more gratings (e.g., applicable to two or more gratings). Three gratings are shown in FIG. 8. With three or more gratings, the local modulation minima within the x-ray diffraction orders is due to the constructive and destructive interference of the radiation diffracted by the three (or more) gratings. The displacement of the minima would simply be correlated to two or more overlay error parameters (depending on whether there were three or more gratings). In the case of three gratings, the minima shift would be correlated with a first overlay error between the top and middle gratings and a second overlay error between the middle and bottom gratings, as well as a third overlay error between the top and bottom gratings.

Figure 9:
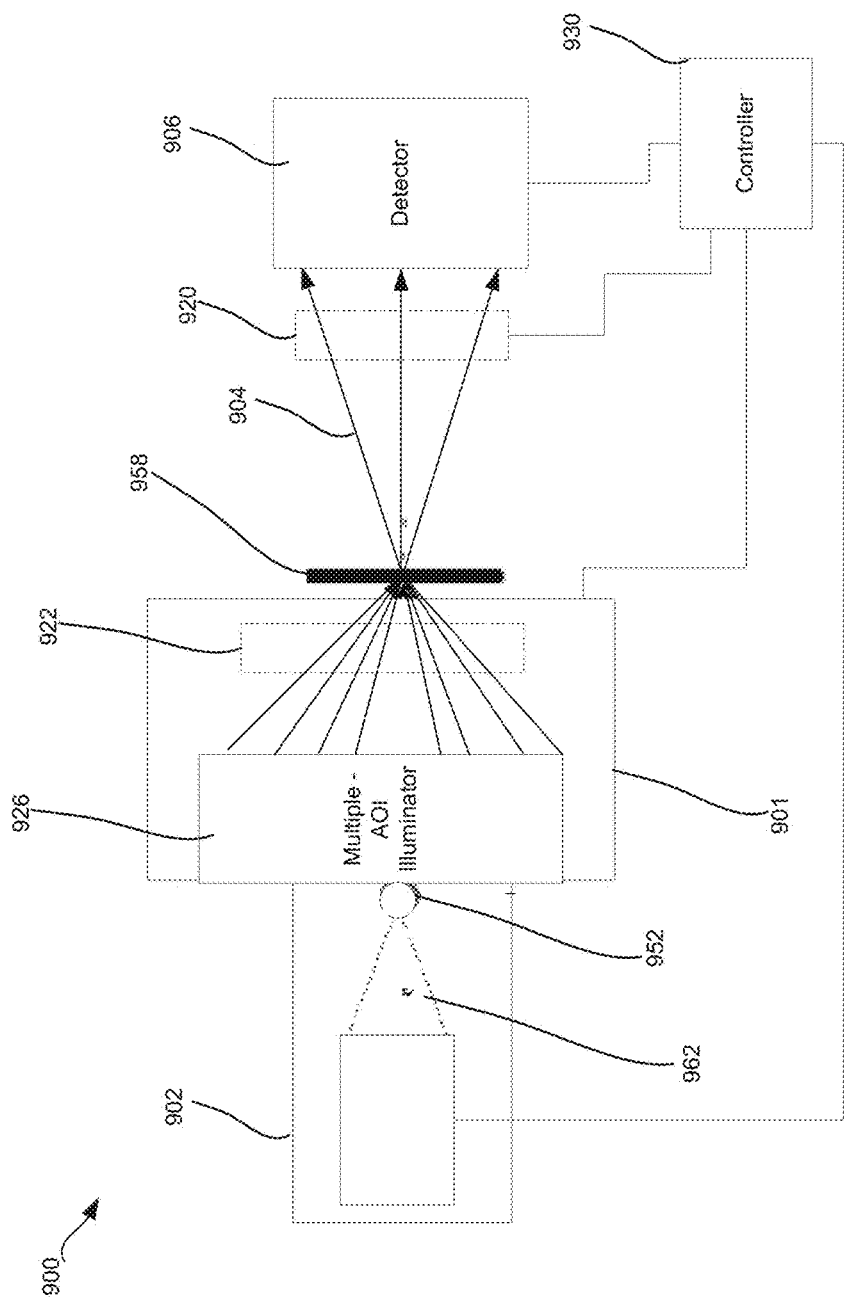
FIG. 9 is a diagrammatic representation of a transmission small angle x-ray scattering (T-SAXS) metrology system in accordance with one embodiment of the present invention.

The techniques of the present invention can be implemented on any suitable x-ray metrology tool that is configured to collect scattered x-rays that are produced from multiple AOI x-rays. As an alternative embodiment, a system that employs multiple, simultaneous AOI x-rays may be utilized. FIG. 9 is a diagrammatic representation of SAXS metrology system 900 in accordance with one embodiment of the present invention. The system 900 may include any suitable illumination system 901 for producing x-rays with multiple AOI's. Additionally, the SAXS system 900 may include one or more high brightness x-ray sources 902, including anode 952 excited by electron beam 962, with suitable x-ray photon energies for generating the X-rays that are incident on the sample 958. A high brightness x-ray source may include a solid anode X-ray source, a liquid metal jet X-ray source, and liquid droplet X-ray source, or other bright x-ray sources such as an Inverse-Compton x-ray source. Example embodiments of a liquid metal jet X-ray source are described is U.S. Pat. No. 7,929,667, which is incorporated herein by reference in its entirety.

In the illustrated embodiment of FIG. 9, the x-ray beams may be collected and reflected or refracted by a multiple-AOI illuminator 926 to produce multiple ranges of AOI's on the sample 958. The multiple-AOI illuminator 926 may take any suitable form. In a specific implementation, the x-rays are reflected from a plurality of grazing incidence X-ray mirrors towards a same point on the sample 108. One of the ways to focus and monochromatize an x-ray beam is through the use of multilayer mirrors. The mirrors are based upon the principle of constructive interference of waves at the interface of a stack of thin layers of alternating materials, for example, in the form of grazing mirrors. Grazing multiple-layer reflecting mirrors that are arranged to reflect at a plurality of AOIs are further described in U.S. patent application Ser. No. 14/515,322, filed 15 Oct. 2014, by Michael S. Bakeman et al., which application is incorporated herein by reference. In general, the grazing mirrors can be sized and arranged to meet the Bragg relation and collect and reflect x-rays in $2\pi$ (or $\varphi$) portions that are $\Delta\theta$ wide. That is, each collection optics (e.g., grazing mirror) may be positioned and sized to collect a particular solid angle of the X-rays. Only light that is produced in a particular cone is going to be incident on each grazing mirror. In alternative embodiments, the multiple-AOI illuminator 926 may be in the form of multilayer Laue lenses, multiple Fresnel zone plate lenses or polycapillary optics to produce multiple beams at different AOIs. In principle, any type of optics (such as Bragg-Fresnel lenses, curved crystals, Wolter optics, etc.) can be employed to achieve different AOIs. An x-ray zone plate may be formed by concentric circles of interleaved material and air to refract x-rays to a focus point at multiple AOIs. By way of an implementation example, multiple capillary x-ray optics or zone plates can be aligned around one or more x-ray sources to produce a number of collimated beams that simultaneously interact with the sample.

Other aspects of the illumination system 901 can include multiple $0^{th}$ order beam blocks (e.g., 920), which can be computer controlled and modular. In some cases, the $0^{th}$ order scattering can have a large associated brightness that may damage the detector if not blocked. The illumination system can include differently sized and shaped blocks for specific applications when different x-ray optics produce beams of varying spot size and divergence. For instance, in the case in which the x-ray optics have low divergence in a single axis and a very large divergence in an orthogonal axis, the $0^{th}$ order beam block, rather than being circular and symmetric, could be rectangular or ellipsoidal, in order to compensate for the beam that has a low divergence in one axis and a large divergence in the other. Likewise, when multiple beams at different AOIs are incident on the wafer in parallel, multiple beam blocks would be used, with each $0^{th}$ order beam block having the proper size and shape to block its particular beam. Different block sizes and shapes can be moved in and out (or rotated in and out) of the $0^{th}$ order beam path, depending on the beam optics configuration. Each block may be formed from a material that substantially blocks the $0^{th}$ order beam. Example materials include lead and tungsten.

Other improvements include different sized pinholes (e.g., 922) for the beams at different AOIs to keep the spot size the same or control beam divergence for the different angles of incidence, and these pinholes can also be computer controlled and modular. For instance, in the case where x-ray optics with low divergence in a single axis and a very large divergence in an orthogonal axis are used, the pinholes, rather than being circular and symmetric, could be rectangular or ellipsoidal, in order to compensate for the beam which has a low divergence in one axis and a large divergence in the other. Likewise, when multiple beams at different AOIs are incident on the wafer in parallel, multiple sets of pinholes would be used, with each set of pinholes having the proper size and shape to produce the desired beam size and divergence for its particular beam.

The scattered x-rays 904 are collected by an x-ray detector 906. A sample handler holds the sample 958 and translates, as well as rotates, the sample 958 for positioning and alignment and to produce angularly resolved scattered x-rays 904. However, since the multiple-AOI illuminator 926 provides multiple AOI's simultaneously, the sample does not need to be tilted to achieve different AOI's (sequentially). As a result, the illumination and collection sides of system 900 are arranged together, provide incident x-rays, and collect and detect scattered x-rays at multiple, simultaneous AOI's to thereby achieve significant improvement in throughput.

The multiple-AOI illuminator 926 and any associated components 922, such as pinholes or apertures, can be computer controlled (e.g., via controller 930) and enable the ability to choose AOIs based upon the sample characteristics.

The detector can be any suitable sensor for detecting scattered x-rays and generating a resulting spectra or image. By way of examples, the sensor can include one or more of the following: a photodiode array, a Charged Coupled Device (CCD), image plate, a hybrid pixel CCD, etc. The detector generally produces an intensity signal that can then be converted to an image by the detector (or controller 930).

Scatterless pinholes or apertures in which a single crystal is bonded to the edges of the pinholes or apertures can be used to reduce parasitic scattering of the beam. This pinhole arrangement can reduce the background noise of the SAXS measurements, increasing the signal to noise and thereby increasing the throughput. A calibration sample, such as Glassy Carbon, or simply a photon counting detector can be utilized to get the absolute photon count on the sample. The calibration results can be used to obtain scattering intensity curves on an absolute scale, rather than a relative scale, which can in certain instances improve the fitting and improve the precision and accuracy of certain geometric parameters. The x-ray intensity calibration can be accomplished using a photodiode or other detector mounted into the pinholes or apertures. Likewise, the x-ray intensity calibration can be accomplished using a photodiode or other detector mounted into the $0^{th}$ order beam block.

Different sized or types of pinholes can be dynamically switched into the illumination and/or collection path. In one example, the illumination optics are designed to have an arrangement that results in an upper limit of divergence and spot size. Pinhole or aperture structures can then be used to block portions of the illumination beams so as to achieve lower divergence beams and smaller spots sizes for particular target structures.

Figure 10:
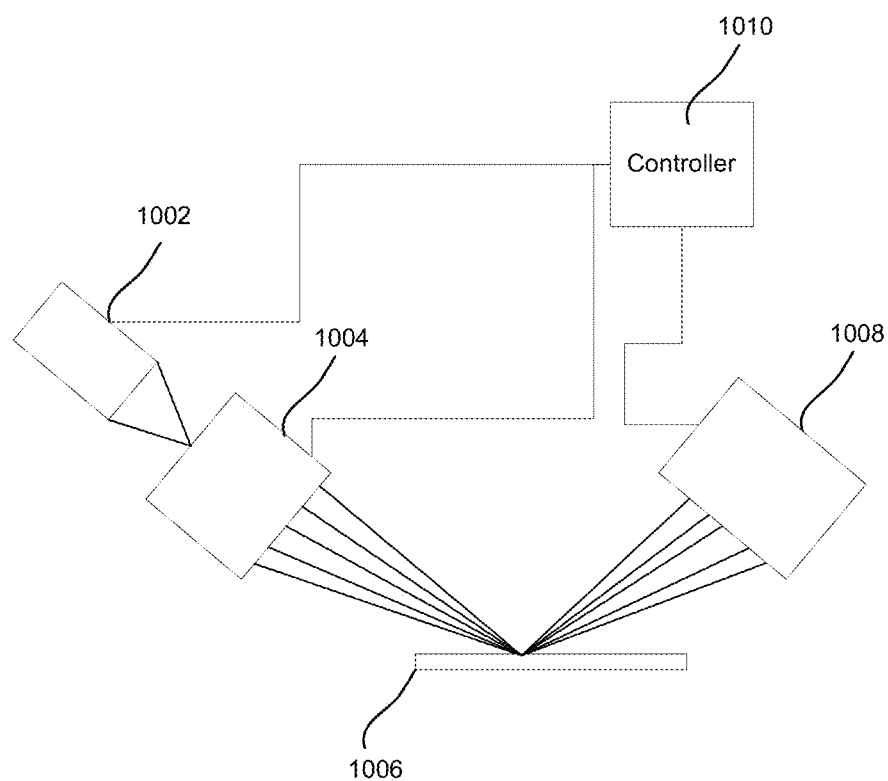
FIG. 10 is a diagrammatic representation of a grazing incidence small-angle x-ray scattering (GI-SAXS) system in accordance with an alternative embodiment of the present invention.

It should be noted that while the illumination and collection systems are described herein with respect to transmission SAXS, this does not preclude the use of these same illumination and collection systems for use with Grazing Incidence SAXS (GI-SAXS) for semiconductor metrology. FIG. 10 is a diagrammatic representation of a GI-SAXS system in accordance with an alternative embodiment of the present invention. As shown, an x-ray source 1002 generates x-rays that are collected and reflected/refracted by illumination optics 1004 onto the sample 1006 at multiple AOIs. X-rays are scattered from the sample 1006 onto detector 1008. The system also includes a controller 1010 for controlling the various components of the GI-SAXS system.

The GI-SAXS system can include multiple sets of optics, pinholes, slits, detectors, and beam blocks that are each optimized for different energies. Since GI-SAXS, in contrast to T-SAXS, does not need higher energy x-rays to penetrate the wafer substrate, x-ray sources with multiple energies, including lower energies, could be used such as liquid metal alloys of Indium Gallium and Tin.

In another embodiment, curved crystals can be used. Crystalline lattice planes can be chosen (such as <111>, <222>, <333> etc.), which provide much smaller periods (d), than are available with multilayer materials. With these much smaller periods, the reflectivity at larger angles of incidence is increased. At very small crystalline lattice parameters, angles of incidence much closer to normal can produce high reflectivity. Two curved crystals with the appropriately chosen lattice planes could be formed to produce a Schwarzschild objective with high reflectivity at x-ray energies of 15 keV. For example, a primary crystalline mirror can be arranged to receive x-rays and refract them to secondary crystalline mirrors, which then refract the x-rays to a focus point. A curved crystal Schwarzschild objective would increase the solid angle of collection over conventional x-ray optics, thus, increasing the photon flux on the sample and increasing the throughput.

For instance, in the case of cubic crystals the distance between lattice planes, d, is given by:

$$\frac{1}{d^2} = \frac{h^2 + k^2 + l^2}{a^2}$$

where h, k, and l are the Miller indices and a is the lattice constant of the crystal. For Silicon with a lattice constant of 5.43 Å, the d-spacing of the <333> plane is 1.045 Å. For a conventional x-ray source such as Mo kα, the wavelength λ is 0.71 Å. Using this wavelength in the Bragg formula:

$$\lambda = 2d \sin \theta$$

with the d-spacing of 1.045 Å, the first Bragg reflection is at 19.86°. Likewise Chromium has a lattice constant of 2.91 Å, giving the d-spacing of the <333> plane a value of 0.56 Å and a Bragg angle of 39.34° for the same case of Mo kα radiation. In this case, the <333> plane of Silicon or Chromium could be grown epitaxially on a curved substrate, or on a flat substrate which is then curved.

In sum, different crystal materials with different lattice plane orientations could be used to provide different d spacings and resulting AOIs for particular wavelengths. Accordingly, this type of crystalline illumination system can be used for optical systems with large acceptance angle ranges.

Other example systems include a wide angle x-ray scattering (WAXS) system, an x-ray diffraction (XRD) system, grazing incidence x-ray diffraction (GIXRD) system, a high resolution x-ray diffraction (HRXRD) system, etc.

It should be recognized that the various steps described throughout the present disclosure may be carried out by a controller, such as single processor system or, alternatively, a multiple processor system. Moreover, different subsystems of the system may include a computer system suitable for carrying out at least a portion of the steps described herein. Therefore, the aforementioned description should not be interpreted as a limitation on the present invention but merely an illustration. Further, the one or more controller system may be configured to perform any other step(s) of any of the method embodiments described herein.

In addition, the controller system may be communicatively coupled to a detector system in any manner known in the art. For example, the controller system may be coupled to computing systems associated with the detector system. In another example, the detector system may be controlled directly by a single computer system coupled to the controller system.

The controller system of the metrology system may be configured to receive and/or acquire data or information from the subsystems of the system by a transmission medium that may include wireline and/or wireless portions. In this manner, the transmission medium may serve as a data link between the controller system and other subsystems of the system.

The controller system of the metrology system may be configured to receive and/or acquire data or information (e.g., measurement spectra or images, $Q_x$ and $Q_z$ mapping data, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the controller system and other systems (e.g., memory on-board metrology system, external memory, reference measurement source, or other external systems). For example, the controller system may be configured to receive measurement data from a storage medium (e.g., internal or external memory) via a data link. For instance, spectral results obtained using the detection system may be stored in a permanent or semipermanent memory device (e.g., internal or external memory). In this regard, the spectral results may be imported from on-board memory or from an external memory system. Moreover, the controller system may send data to other systems via a transmission medium. For instance, qualitative and/or quantitative results determined by processor system may be communicated and stored in an external memory. In this regard, measurement results may be exported to another system.

The controller system may include, but is not limited to, a personal computer system, mainframe computer system, workstation, image computer, parallel processor, or any other device known in the art. In general, the term "processor system" may be broadly defined to encompass any device having one or more processors, which execute instructions from a memory medium. Program instructions implementing methods such as those described herein may be transmitted over a transmission medium such as a wire, cable, or wireless transmission link. Program instructions may be stored in a computer readable medium (e.g., memory). Exemplary computer-readable media include read-only memory, a random access memory, a magnetic or optical disk, or a magnetic tape.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be configured in firmware, software, FPGA, programmable optics components, etc.

The data analysis and fitting steps may be used to pursue one of the following goals: measurement of CD, SWA, shape, stress, focus/dose, overlay, and/or any combination thereof; modeling and/or design of metrology systems; and modeling, design, and/or optimization of metrology targets.

Certain embodiments of the present invention presented here generally address the field of semiconductor metrology and process control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the techniques can be applied to other types of samples, beside semiconductor wafers, such as reticles. Accordingly, the present embodiments are to be considered as illustrative and not restrictive, and the invention is not to be limited to the details given herein.

What is claimed is:

1. A method for determining overlay error in a semiconductor target, the method comprising:
   for illumination x-rays having a plurality of angles of incidence (AOI), obtaining a correlation model that correlates overlay error of a target with a plurality of intensity diffraction patterns, one for each AOI, for x-rays scattered from the target in response to the illumination x-rays;
   illuminating a first target with illumination x-rays having a plurality of AOI and collecting x-rays that are scattered in a plurality of intensity diffraction patterns, one for each AOI, from the first target in response to the illumination x-rays at the plurality of AOI; and
   determining an overlay error of the first target based on the plurality of intensity diffraction patterns of the x-rays collected from the first target and the correlation model.

2. The method of claim 1, wherein the overlay error is determined by correlating overlay error with relative positions of intensity minimum along a Qz axis for a plurality of diffraction orders of the intensity diffraction patterns collected from the first target, wherein the Qz axis is perpendicular to a one of the intensity diffraction patterns collected for a normal AOI and the Qz axis together with a Qx axis form a Qz-Qx space into which the plurality of intensity diffraction patterns are fanned out relative to each other based on their relative AOI.

3. The method of claim 1, wherein the correlation model is determined by a neural network or a principal component analysis.

4. The method of claim 1, wherein the first target is aperiodic.

5. The method of claim 1, wherein the overlay is determined for a first direction, the method further comprising repeating the operations for illuminating and determining a second overlay error in a second direction that differs from the first direction.

6. The method of claim 1, wherein illuminating at the plurality of AOI is accomplished simultaneously.

7. The method of claim 1, wherein illuminating at the plurality of AOI is accomplished sequentially.

8. The method of claim 1, wherein the first target comprises two or more vertically stacked gratings.

9. The method of claim 1, wherein the first target is designed to have pitch and critical dimension values that meet device design rule specifications.

10. The method of claim 9, wherein the first target is located in an active device and in-die area.

11. The method of claim 1, wherein illuminating and collecting are performed by a transmission small-angle x-ray scattering (T-SAXS) system, a grazing incident small-angle x-ray scattering (GI-SAXS) system, a wide angle x-ray scattering (WAXS) system, an x-ray diffraction (XRD) system, grazing incidence x-ray diffraction (GIXRD) system, or a high resolution x-ray diffraction (HRXRD) system.

12. The method of claim 1, wherein the overlay error is determined by correlating overlay error with a length of a distribution of intensity values along a Qz axis, which together with a Qx axis form a Qz-Qx space into which the plurality of intensity diffraction patterns are fanned out relative to each other based on their relative AOI.

13. A semiconductor metrology system, comprising:
   an x-ray source for generating x-rays;
   illumination optics for collecting and reflecting or refracting a portion of the generated x-rays towards a particular focus point on a semiconductor sample in the form of a plurality of incident beams at a plurality of different angles of incidence (AOI);
   a sensor for collecting output x-ray beams that are scattered from the sample in response to the incident beams on the sample at the different AOI; and
   a controller configured for performing the following operations:
      for illumination x-rays having a plurality of angles of incidence (AOI), obtaining a correlation model that correlates overlay error of a target with a plurality of intensity diffraction patterns, one for each AOI, for x-rays scattered from the target in response to the illumination x-rays;
      causing the illumination optics to illuminate a first target with illumination x-rays at a plurality of AOI and collecting x-rays that are scattered in a plurality of intensity diffraction patterns, one for each AOI, from the first target in response to the illumination x-rays at the plurality of AOI; and
      determining an overlay error of the first target based on the plurality of intensity diffraction patterns of the x-rays collected from the first target and the correlation model.

14. The system of claim 13, wherein the illumination optics and sensor are arranged to form a transmission small-angle x-ray scattering (T-SAXS) system.

15. The system of claim 13, wherein the illumination optics and sensor are arranged to form a grazing incident small-angle x-ray scattering (GI-SAXS) system.

16. The system of claim 13, further comprising a stage that is positionable in relation to the illumination optics to achieve the different AOIs.

17. The system of claim 13, wherein the overlay error is determined by correlating overlay error with relative positions of intensity minimum along a Qz axis for a plurality of diffraction orders of the intensity diffraction patterns collected from the first target, wherein the Qz axis is perpendicular to a one of the intensity diffraction patterns collected for a normal AOI and the Qz axis together with a Qx axis form a Qz-Qx space into which the plurality of intensity diffraction patterns are fanned out relative to each other based on their relative AOI.

18. The system of claim 13, wherein the correlation model is determined by a neural network or a principal component analysis.

19. The system of claim 13, wherein illuminating at the plurality of AOI is accomplished simultaneously.

20. The system of claim 13, wherein illuminating at the plurality of AOI is accomplished sequentially.

21. The system of claim 13, wherein the first target comprises two or more vertically stacked gratings.

22. The system of claim 13, wherein the overlay error is determined by correlating overlay error with a length of a distribution of intensity values along a Qz axis, which together with a Qx axis form a Qz-Qx space into which the plurality of intensity diffraction patterns are fanned out relative to each other based on their relative AOI.

* * * * *